(12) United States Patent
Manocchio et al.

(10) Patent No.: US 11,364,350 B2
(45) Date of Patent: Jun. 21, 2022

(54) SAFETY PEN NEEDLE VARIABLE INDICATOR

(71) Applicant: Embecta Corp., Andover, MA (US)

(72) Inventors: John Manocchio, River Edge, NJ (US); Mark Bowen, Stow, MA (US); Kunjal Oza, North Brunswick, NJ (US); Louis Vieira, Milford, CT (US)

(73) Assignee: Embecta Corp., Andover, MA (US)

( * ) Notice: Subject to any disclaimer, the term of this patent is extended or adjusted under 35 U.S.C. 154(b) by 213 days.

(21) Appl. No.: 16/603,990

(22) PCT Filed: Apr. 4, 2018

(86) PCT No.: PCT/US2018/026078
§ 371 (c)(1),
(2) Date: Oct. 9, 2019

(87) PCT Pub. No.: WO2018/191076
PCT Pub. Date: Oct. 18, 2018

(65) Prior Publication Data
US 2020/0114090 A1 Apr. 16, 2020

Related U.S. Application Data

(63) Continuation of application No. 62/483,629, filed on Apr. 10, 2017.

(51) Int. Cl.
*A61M 5/32* (2006.01)
*A61M 5/24* (2006.01)

(52) U.S. Cl.
CPC .......... *A61M 5/3243* (2013.01); *A61M 5/24* (2013.01); *A61M 2005/3247* (2013.01); *A61M 2205/3561* (2013.01); *A61M 2205/3584* (2013.01)

(58) Field of Classification Search
CPC .......... A61M 5/3243; A61M 5/24; A61M 2005/3247; A61M 2205/3561;
(Continued)

(56) References Cited

U.S. PATENT DOCUMENTS 6,805,686 B1 10/2004 Fathallah et al.
8,728,027 B2 5/2014 Jensen et al.
(Continued)

FOREIGN PATENT DOCUMENTS

CN 103228306 A 7/2013
EP 2514450 A1 10/2012
(Continued)

*Primary Examiner* — Theodore J Stigell
*Assistant Examiner* — Rachel T. Smith
(74) *Attorney, Agent, or Firm* — Greenberg Traurig, LLP; David J. Dykeman; Roman Fayerberg

(57) ABSTRACT

A safety pen needle assembly (12) is disclosed which comprises a hub (30), a needle cannula (20) engaged to the hub (30), the needle cannula (20) having a distal end for insertion into a patient, and a proximal end extending into the hub (30), a sleeve (14) surrounding the hub (30) and needle cannula (20), a shield (16) including a window (18), the shield (16) surrounding the sleeve (14) and movable relative to the sleeve (14) from a first position, to a second position and to a third position to expose and cover the distal end of the needle cannula (20), and a spring (144) urging the shield (16) to move relative to the sleeve (14) from the second position to the third position, wherein the window (18) indicates when the needle cannula (20) is extended in the second position.

16 Claims, 9 Drawing Sheets

(58) Field of Classification Search
CPC ........ A61M 2205/3584; A61M 5/3245; A61M 5/3202; A61M 2205/583; A61M 2205/584; A61M 2005/3267; A61M 5/3275

See application file for complete search history.

(56)  References Cited

U.S. PATENT DOCUMENTS

| | | | |
|---|---|---|---|
| 9,504,791 | B2 | 11/2016 | Cross et al. |
| 2002/0004648 | A1* | 1/2002 | Larsen ................ A61M 5/3272 128/919 |
| 2002/0133122 | A1 | 9/2002 | Giambattista et al. |
| 2003/0120209 | A1 | 6/2003 | Jansen et al. |
| 2005/0096598 | A1* | 5/2005 | Crawford .............. A61M 5/326 604/198 |
| 2013/0041321 | A1 | 2/2013 | Cross et al. |
| 2013/0237932 | A1 | 9/2013 | Thueer et al. |
| 2014/0058333 | A1 | 2/2014 | Cross et al. |
| 2018/0110935 | A1* | 4/2018 | Carroll .................... A61M 5/24 |
| 2018/0353703 | A1* | 12/2018 | Wendland ......... A61M 5/31546 |

FOREIGN PATENT DOCUMENTS

| | | | |
|---|---|---|---|
| JP | 2012130732 A | 7/2012 | |
| WO | 0191837 A1 | 12/2001 | |
| WO | 2003045480 A1 | 6/2003 | |
| WO | 2009114777 A1 | 9/2009 | |
| WO | 2011117284 A1 | 9/2011 | |
| WO | 2012072563 A1 | 6/2012 | |
| WO | 2012143439 A1 | 10/2012 | |
| WO | 2016180873 A1 | 11/2016 | |
| WO | WO-2016180873 A1 * | 11/2016 | ........ A61M 5/31553 |

* cited by examiner

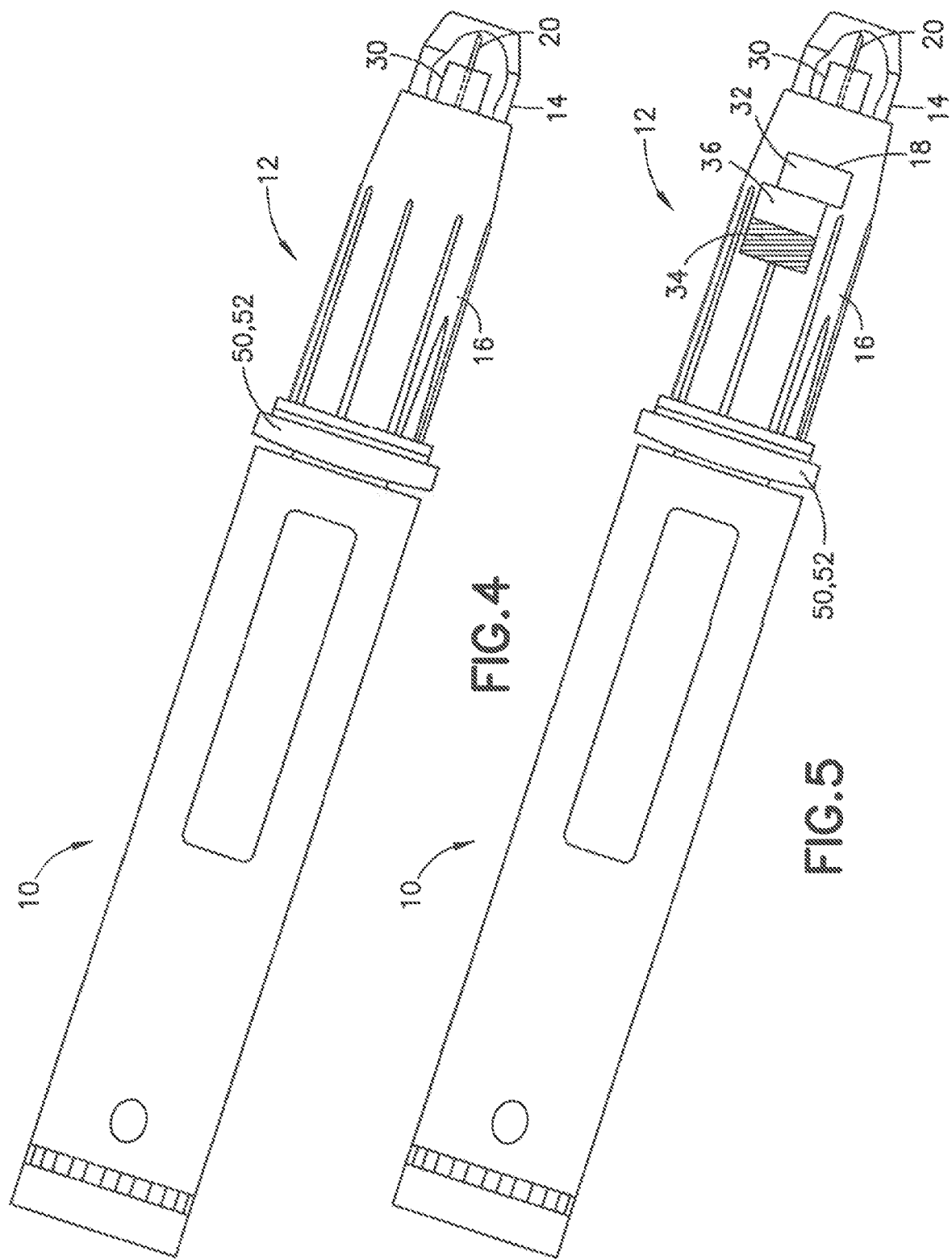

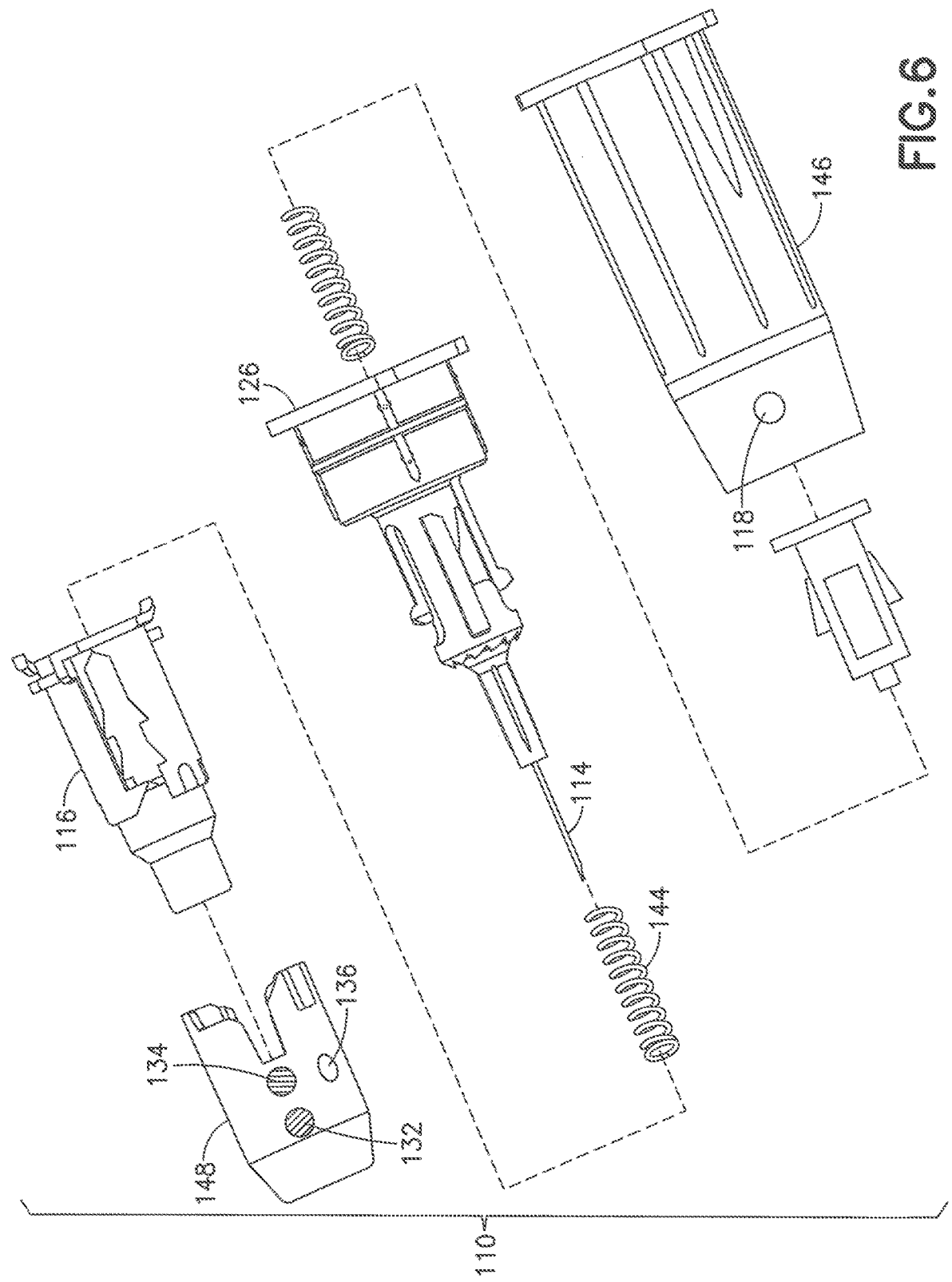

SAFETY PEN NEEDLE VARIABLE INDICATOR

This application claims the benefit under 35 U.S.C. § 119(e) of a U.S. Provisional Application Ser. No. 62/483,629, filed on Apr. 10, 2017.

FIELD

This invention relates to safety pen needle assemblies.

BACKGROUND

Safety pen needle assemblies are well known in the art for use with medical injectors, particularly medication delivery pen injectors. Shielding of a used needle before and after injection is provided by such devices. However, it can be difficult for a health care professional to confirm needle exposure or needle injection as well as provide safety activation. As such, a user may inadvertently inject prematurely or experience a false injection.

Transmission of biological material or disease is not a concern with the needle being in a clean state; however, a safety activation mechanism can prevent the health care professional or a patient from suffering an incidental needle stick. The safety pen needle must be properly disposed of since the needle cannot be used subsequently on a patient.

SUMMARY OF THE INVENTION

It is an aspect of the present invention to provide a variable indicator on a safety pen needle to indicate needle cannula exposure and safety activation. Such a safety pen needle provides advantages in informing the health care professional that the needle cannula is extended and injected into a skin of the patient. Also, the safety pen needle provides a safety activation lock to prevent the needle cannula from further exposure or contamination after use.

The foregoing and/or other aspects of the present invention can be achieved by providing a safety pen needle assembly comprising a hub, a needle cannula engaged to the hub, the needle cannula having a distal end for insertion into a patient, and a proximal end extending into the hub, a sleeve surrounding the hub and needle cannula, a shield including a window, the shield surrounding the sleeve and movable relative to the sleeve from a first position, to a second position and to a third position to expose and cover the distal end of the needle cannula, and a spring urging the shield to move relative to the sleeve from the second position to the third position, wherein the window indicates when the needle cannula is extended in the second position.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 4 illustrates a perspective view of a second exemplary embodiment of a safety pen needle with a smart ring connected to a medication delivery pen;

FIG. 5 illustrates a perspective view of a third exemplary embodiment of a safety pen needle having a window and a smart ring while connected to a medication delivery pen;

FIG. 6 illustrates an exploded perspective view of a fourth exemplary embodiment of a safety pen needle;

DETAILED DESCRIPTION OF EXEMPLARY EMBODIMENTS

Figure 1:
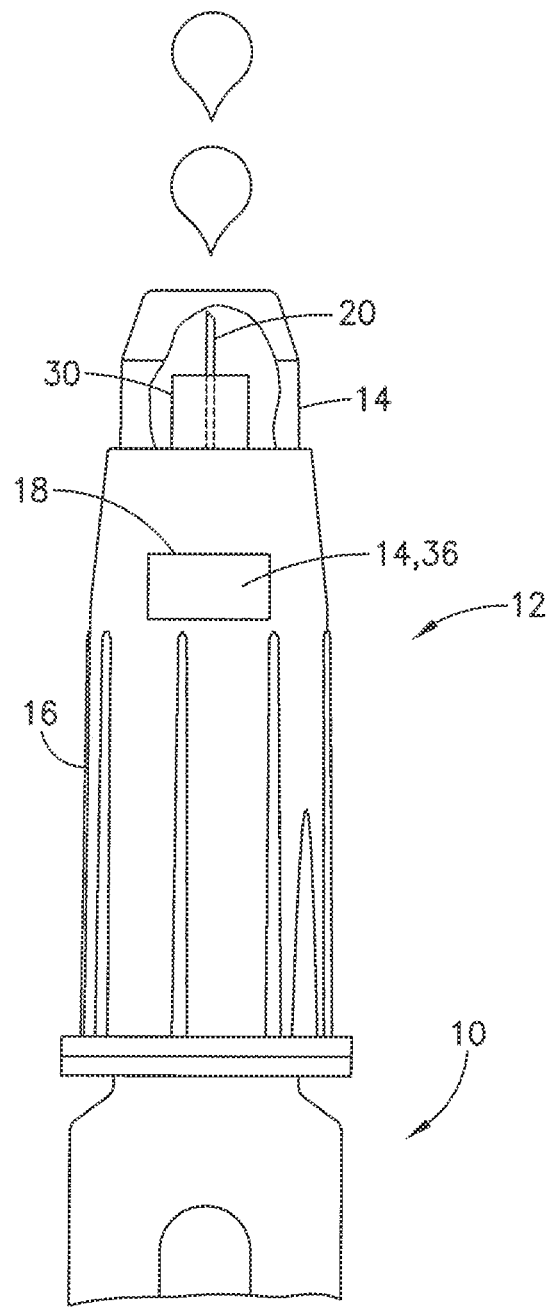
FIG. 1 illustrates a front view of a first exemplary embodiment of a safety pen needle in a first position.

FIG. 1 illustrates a typical medication delivery pen 10 connected to a first embodiment of a safety pen needle 12. The safety pen needle 12 includes a hollow needle cannula 20 engaged to a hub 30. The needle cannula 20 includes a sharpened distal end that injects and dispenses medicament to a patient and a proximal end that is in fluid communication with a vial, cartridge or reservoir within the medication delivery pen 10.

The needle cannula 20 is engaged to the hub 30 and extends beyond a proximal end of the hub 30 at all stages of operation. In one embodiment, the hub 30 includes indicia such as colors, numbers, patterns (such as stripes or spots), textures and/or symbols to indicate needle cannula exposure. Further explanation of the indication of needle cannula exposure is described below.

The hub 30 is surrounded by a movable sleeve 14. A distal end of the sleeve 14 provides a stopping surface when the needle cannula 20 contacts a skin of a patient. From the distal end of the sleeve 14, the needle cannula 20 is extended and injected into a patient.

Figure 2:
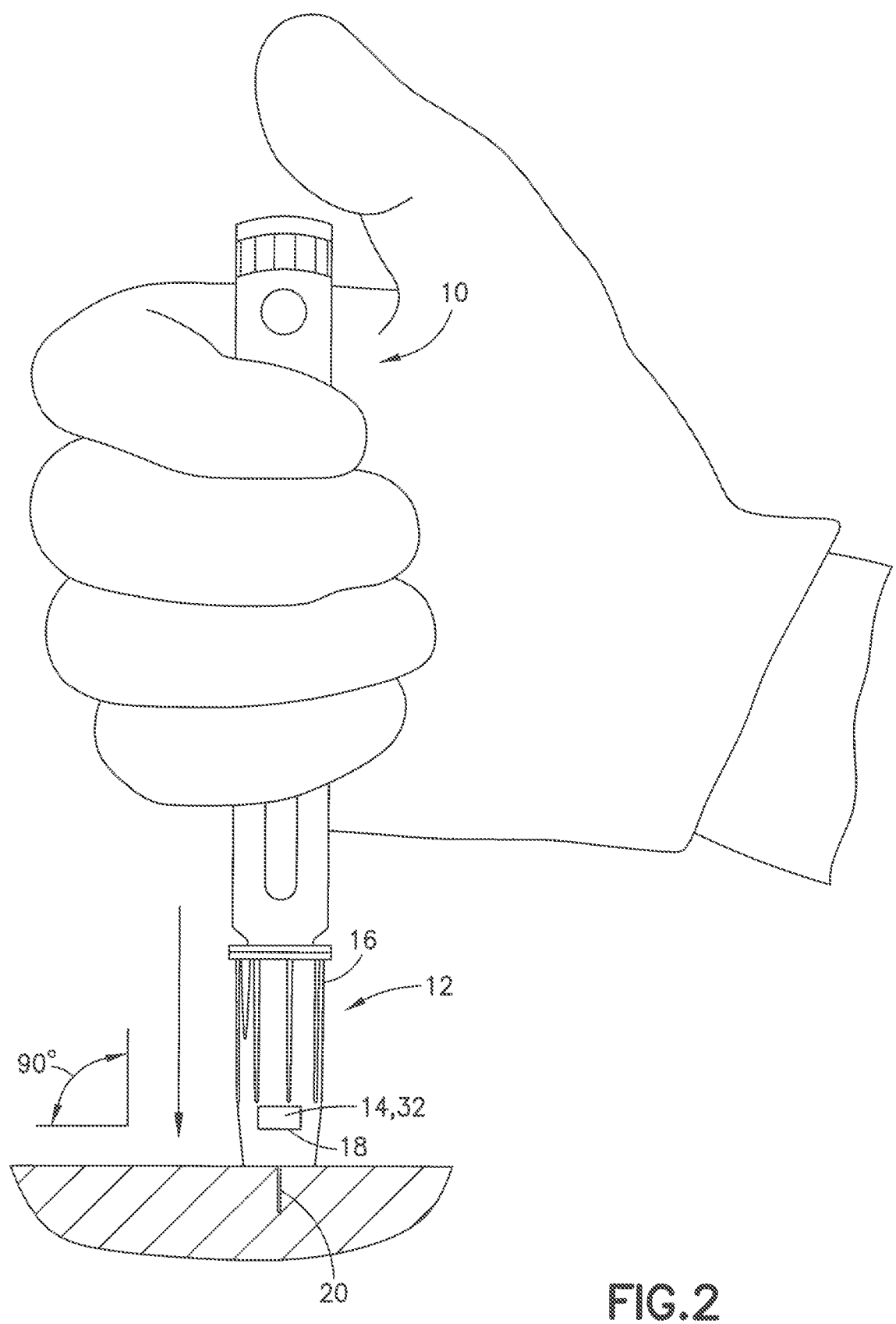
FIG. 2 illustrates a front view of the safety pen needle of FIG. 1 in a second position.
Figure 3:
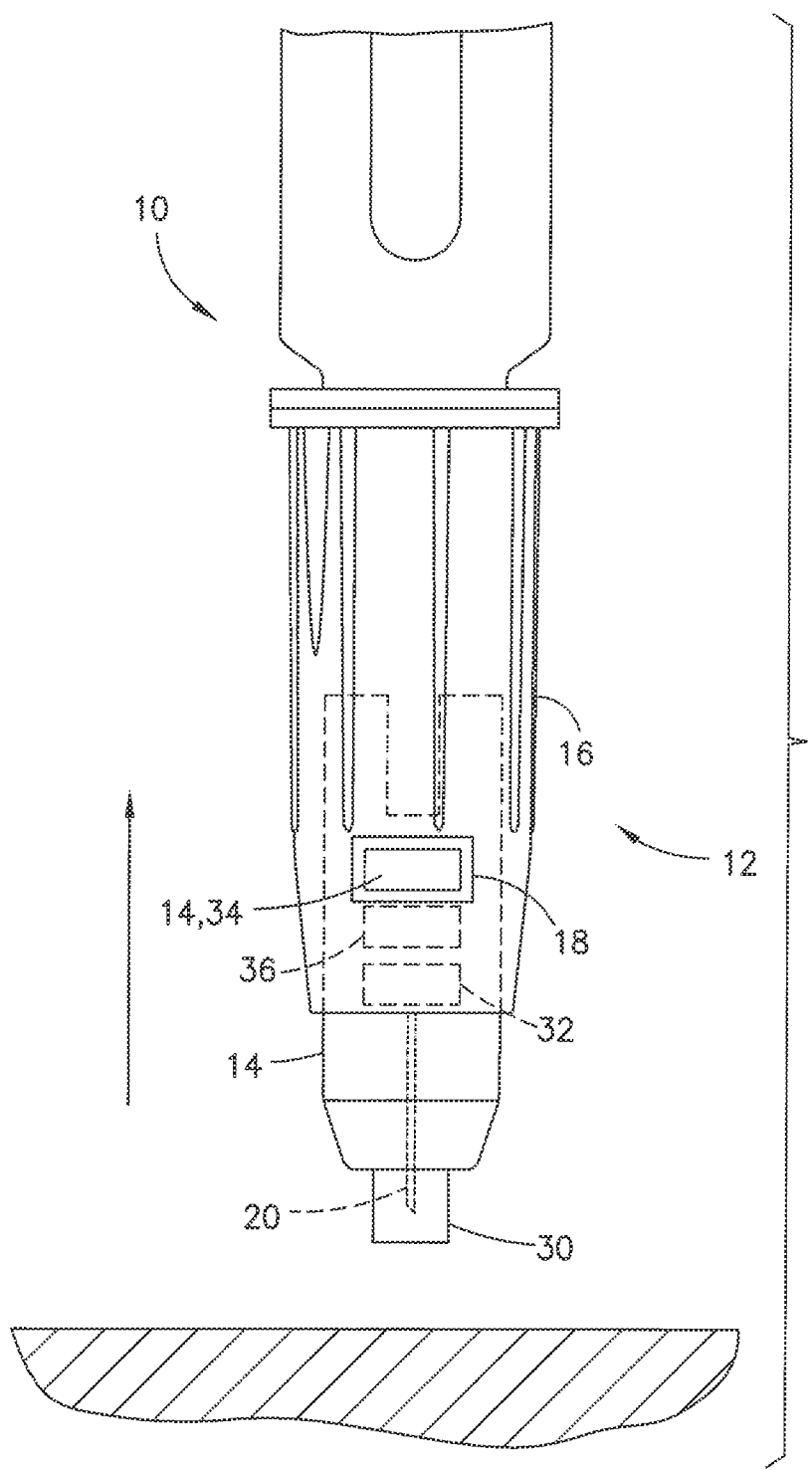
FIG. 3 illustrates a front view of the safety pen needle of FIGS. 1 and 2 in a third position.

In a first position, as illustrated in FIG. 1, when the safety pen needle 12 is ready for operation, the sleeve 14 encloses and surrounds the needle cannula 20 and hub 30. The hub 30 partially encloses the needle cannula 20 in this first position. In a third position, as illustrated in FIG. 3, when the safety pen needle 12 is in a safe mode after use, the sleeve 14 partially encloses and surrounds the needle cannula 20 and hub 30. The hub 30 fully encloses the needle cannula 20 in this third position. However, in a second position, as illustrated in FIG. 2, when the safety pen needle 12 is deployed for medication delivery, the needle cannula 20 extends beyond the hub 30 and the sleeve 14.

In view of the above, the safety pen needle 12 is a single needle cannula 20 device that advantageously hides the needle cannula 20 when not in use (the first and third positions). In other words, the needle cannula 20 is only exposed in the second position during medication delivery. The safety pen needle 12 having; the single needle cannula 20 is also different from a typical pen needle magazine where a plurality of pen needles is provided for use by the medication delivery pen 10.

The sleeve 14 is multicolored and cooperates with a shield 16 to visually indicate the status of the safety pen needle 12 in the first, second and third positions. In another embodiment, the hub 30 and shield 16 can also cooperate together to display the status of the safety pen needle 12 in a similar manner. The sleeve 14 cooperates with a window 18 in the shield 16 as described below to depict the status of the safety pen needle 12. The window 18 may comprise an opening (cut-out) in the shield 16 with or without a transparent cover.

The sleeve 14 is partially surrounded by the shield 16 in the first and third positions. The shield 16 is movably connected to the hub 30, the needle cannula 20 and the sleeve 14. The shield 16 is also pressurized by a spring (see FIG. 6) to urge the movement of the shield 16.

Specifically, in the first position as illustrated in FIG. 1, the shield 16 is in a ready or retracted position and the spring urges the shield 16 toward the retracted position. However, the shield 16 is in an unlocked state and is free to move. The spring does not prevent the shield 16 from moving. Rather, the health care professional can overcome the spring force to move the shield 16. The shield 16 also partially surrounds the sleeve 14.

In the second position as illustrated in FIG. 2, the health care professional operates the device by pushing down on the medication delivery pen 10 which is connected to the safety pen needle 12. This pressure causes the needle cannula 20 to deploy into the skin of the patient for medication delivery. In this position, the shield 16 is extended and moves to a second position to overcome the pressurized force by the compressed spring. The movement of the shield 16 causes the hub 30 and the needle cannula 20 to move from a retracted position (first position) to an extended position (second position). The shield 16 fully surrounds the sleeve 14, and the needle cannula 20 extends beyond the shield 16 and sleeve 14 in the second position.

In the third position as illustrated in FIG. 3, the health care professional removes the medication delivery pen 10 that is connected to the safety pen needle 12 from the patient. Upon removal, the spring urges the shield 16 to move back to the third position. The sleeve 14 also moves back to expose the hub 30 and the needle cannula 20. However, the needle cannula 20 is fully enclosed in the hub 30 in the third position. Thus, the spring advantageously provides automatic retraction of the shield 16 and the needle cannula 20 after use in the second position as the safety pen needle 12 moves to the third position. Similar to the first position, the shield 16 partially surrounds the sleeve 14.

In the third position, a locking mechanism (see FIG. 7) of the safety pen needle 12 locks the shield 16 and prevents the safety pen needle 12 from further use. Specifically, the needle cannula 20 is fully enclosed by the hub 30 and is unable to be exposed in the second position or return for use in the first position. The locking mechanism may include, for example, a tab on an inner surface of the shield 16 and a slot on an outer surface of the hub 30, although various other configurations are contemplated herein.

According to the first embodiment, the first position and the third position, as illustrated in FIGS. 1 and 3, are different from each other. Specifically, in the third position, the shield 16 and sleeve 14 are in a further retracted position when compared to the first position. According to another embodiment, the first position and the third position are the same position. In this alternate embodiment, the locking mechanism is configured to be used in the third position but not the first position. In another embodiment, the sleeve 14 is rotated to angularly displace the third position from the first and second position.

The shield 16 includes the window 18 which visibly indicates needle cannula exposure and safety activation. Specifically, as illustrated in FIG. 1, the window 18 visually exposes a white portion 36 of the sleeve 14 to represent the ready position. In this first position, the safety pen needle 12 is ready for operation and is in an unlocked state to allow various components to move.

As illustrated in FIG. 2, the window 18 visually exposes a green portion 32 of the sleeve 14 to represent the fully deployed position. In this second position, the needle cannula 20 of the safety pen needle 12 is exposed, inserted into the patient and is dispensing medication. This visual indication advantageously provides the health care professional confirmation that the needle cannula is in the skin of the patient. This visual indication is a significant improvement over a mere tactile notification or needle cannula sensation that the health care professional may previously have relied upon to confirm needle cannula insertion. Another advantage this visual indication provides is less training for health care professionals and reduced risk of injection errors.

As illustrated in FIG. 3, the window 18 visually exposes a red portion 34 of the sleeve 14 to represent the safe mode in the third position. In this third position, the needle cannula 20 is retracted into the hub 30 and is locked from further exposure and use. This visual indication advantageously provides the health care professional notice that the safety pen needle 12 is in safe activation mode. Such an indication protects patients and health care professionals from being contaminated by used needle cannulas.

In other embodiments, alternative types of indicia such as numbers, patterns (such as stripes or spots), textures and/or symbols can replace or supplement the green, red or white portions 32, 34, 36 of the sleeve 14 as described above. Different patterns or textures can advantageously aid those who are blind, color blind or in cases where red/green colors, for example, are perceived differently in other countries. Additionally, in one embodiment, the window 18 can be tinted to adjust what is visually displayed.

FIG. 4 illustrates a second embodiment of the safety pen needle 12 described above having a smart ring 50 but without a window. The smart ring 50 is a circular ring disposed at a proximal end of the safety pen needle 12. When the safety pen needle 12 is engaged to the medication delivery pen 10, the smart ring 50 is disposed between the safety pen needle 12 and the medication delivery pen 10.

The smart ring 50 includes electronics such as electrical contacts or sensors 52 that cooperate with the remaining components of the safety pen needle 12 to sense positional and/or spatial arrangements to determine a position of the shield 16 and dose data. For example, the smart ring 50 is able to determine needle insertion and needle exposure time, needle insertion rate and needle exposure rate, the number of injections performed, time intervals between injections and the number of needles used or available for injection.

The smart ring 50 also determines the position of the shield 16 to identify which of the three positions the safety pen needle 12 is operating in as described above. The smart ring 50 communicates positional data or dose data to an external smart device for monitoring and status notification such as if the safety pen needle 12 is in the first, second or third positions. The external smart device can be, for example, a mobile phone, laptop, iPad, a smart medication delivery pen or other processing device.

The smart ring 50 communicates data wirelessly or via a wireline connection to the external smart device. Different wireless connectivity methods can be used (e.g., Bluetooth™ or Wi-Fi or near field communication (NFC) technology) which can, in turn, impact device pairing if needed and the need for proximity of the external smart device. For example, Bluetooth™ employs a particular device pairing process. The proximity of the two communicating platforms relative to each other depends on the connectivity method used.

FIG. 5 illustrates a third embodiment of the safety pen needle 12 described above having a smart ring 50 and the window 18. This embodiment incorporates the smart ring 50 technology described in the second embodiment, as well as the visual indication feature of the window 18 described in the first embodiment. This configuration advantageously provides data communication and status indication through the window 18 at the same time.

In this embodiment, the sleeve 14 is rotated during operation to angularly displace the second position from the first and third position. Accordingly, the sleeve 14 rotates and axially moves from the first position (white portion 36) to the second position (green portion 32) and displays the status through the window 18. After use, the sleeve 14 rotates and axially moves from the second position (green portion 32) to the third position (red portion 34).

In addition to the advantages described above in the first embodiment, the use of the smart ring 50 in the safety pen needle 12 of the second and third embodiments can prohibit injection until the needle cannula has been fully exposed or fully extended. Such a feature can further mitigate the risk of a failed injection.

FIG. 6 illustrates a fourth embodiment of the safety pen needle 110 that functions in a similar manner as the embodiments described above. Specifically, the safety pen needle 110 includes an outer shield 148 with three colored dots 132, 134, 136 that cooperate with a sleeve 146 having a window 118. The safety pen needle 110 further includes an inner shield 116 and a needle 114 fixed to a needle hub 126 that cooperates with a spring 144 to allow for needle 114 movement between an extended and a retracted position.

The outer shield 148 slides in and out and rotates, depending on the state of the safety pen needle 110. Three dots, white 136, red 134, and green 132 are located on the outer shield 148 such that one of the three dots 132, 134, 136 aligns with the window 118 in the sleeve 146, depending on the state of the safety pen needle 110.

In the ready position (as delivered), the white dot 136 is visible in the window 118. During injection, the outer shield 148 will retract into the sleeve 146 and rotate, bringing the green dot 132 into view in the window 118. In the locked state, the shield 148 will move forward, bringing the red dot 134 into view through the window 118. The spring 144 provides a spring force to return the outer shield 148 of the safety pen needle 110 into the retracted position.

In other embodiments, alternative types of indicia such as numbers, patterns (such as stripes or spots), textures and/or symbols can replace or supplement the green, red or white colored dots 132, 134, 136 of the outer shield 148 as described above. Different patterns or textures can advantageously aid those who are blind, color blind or in cases where red/green colors, for example, are perceived differently in other countries.

Figure 7:
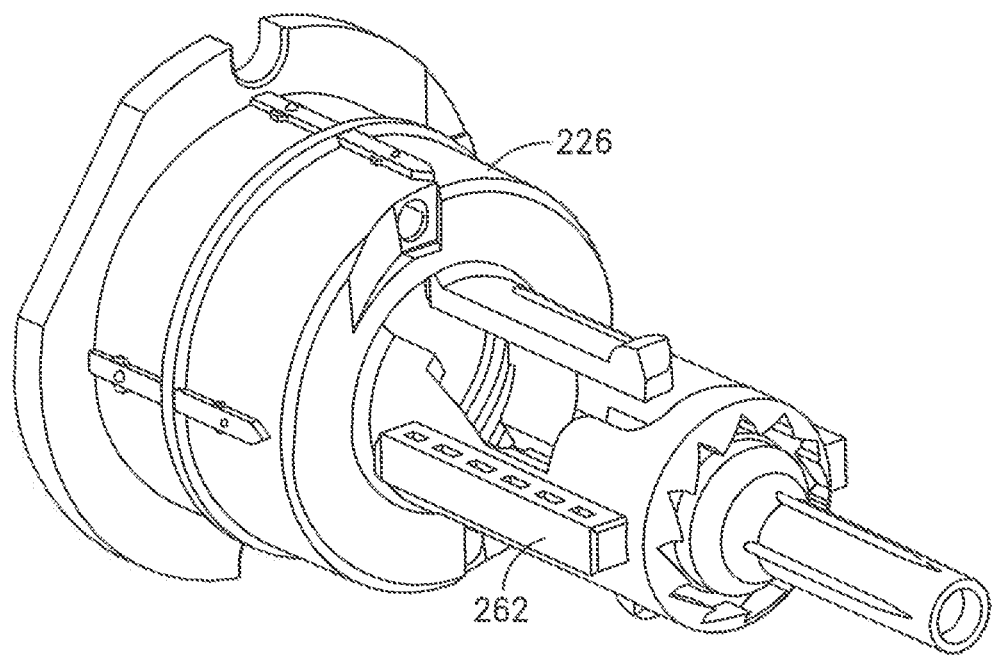
FIG. 7 is a right perspective view of a fifth exemplary embodiment of a safety pen needle with a portion of a locking mechanism on a needle hub.

FIGS. 7-13 illustrate a fifth embodiment of the safety pen needle having a locking mechanism comprising locking rails 262 and slots 264 as described below. FIG. 7 illustrates a needle hub 226 having the locking rails 262. The locking rails 262 are an extruded rectangular member along a longitudinal surface of the needle hub 226. The locking rails 262 are disposed on an outer surface of the needle hub 226 in a substantially central axial position. Two locking rails 262 are disclosed to be equidistant along the outer surface of the needle hub 226, although more or fewer locking rails are contemplated.

Figure 8:
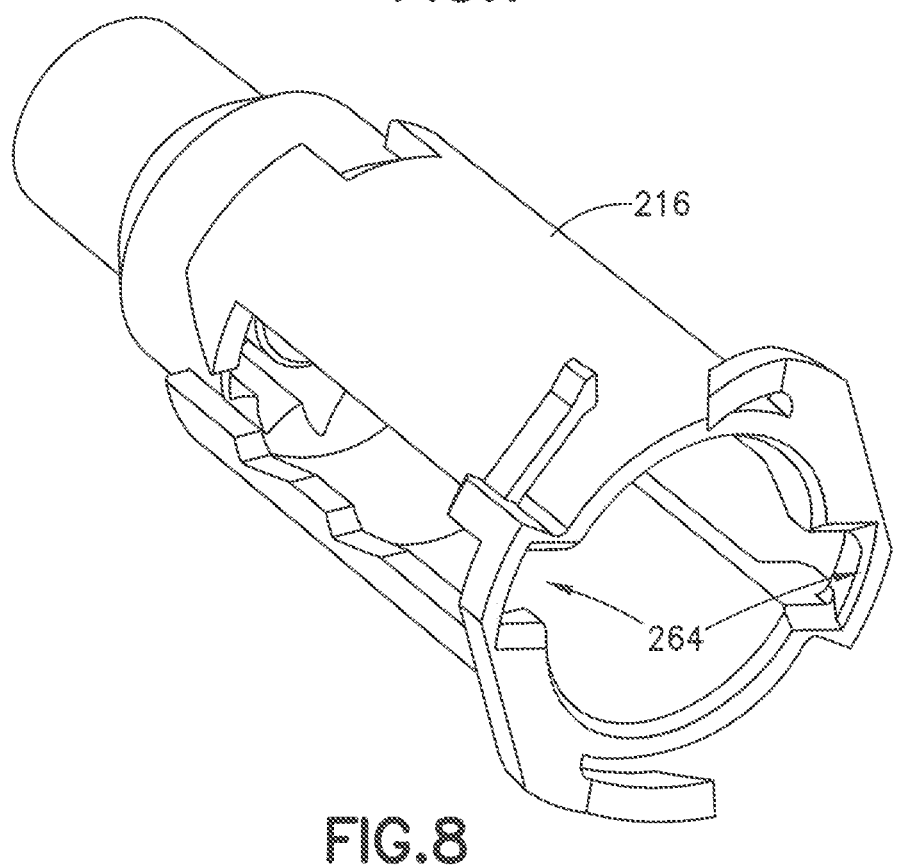
FIG. 8 illustrates a left perspective view of the safety pen needle of FIG. 7 with a portion of the locking mechanism on an inner shield.

FIG. 8 illustrates an inner shield 216 having the slots 264. The slots 264 are internal rectangular cavities disposed at a proximal end surface of the inner shield 216. As the slots 264 extend beyond the proximal end surface at the proximal end of the inner shield 216, the slots 264 are open and exposed along a length of the inner shield 216. The slots 264 are sized to engage the locking rails 262 of the needle hub 226. More or fewer slots 264 are contemplated based on the number of corresponding locking rails 262 in the needle hub 226.

Figure 9:
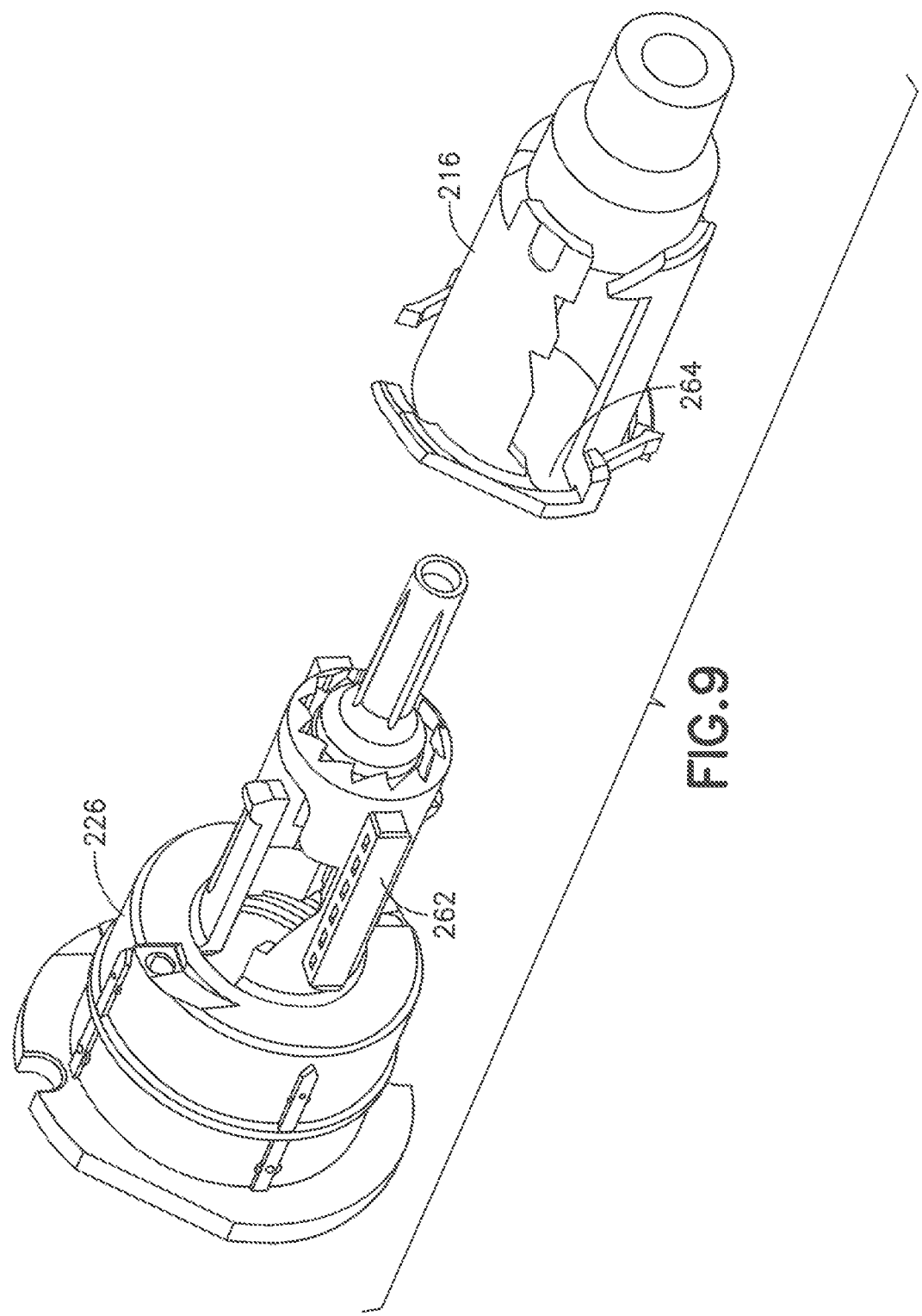
FIG. 9 illustrates an exploded perspective view of the safety pen needle of FIGS. 7 and 8.
Figure 10:
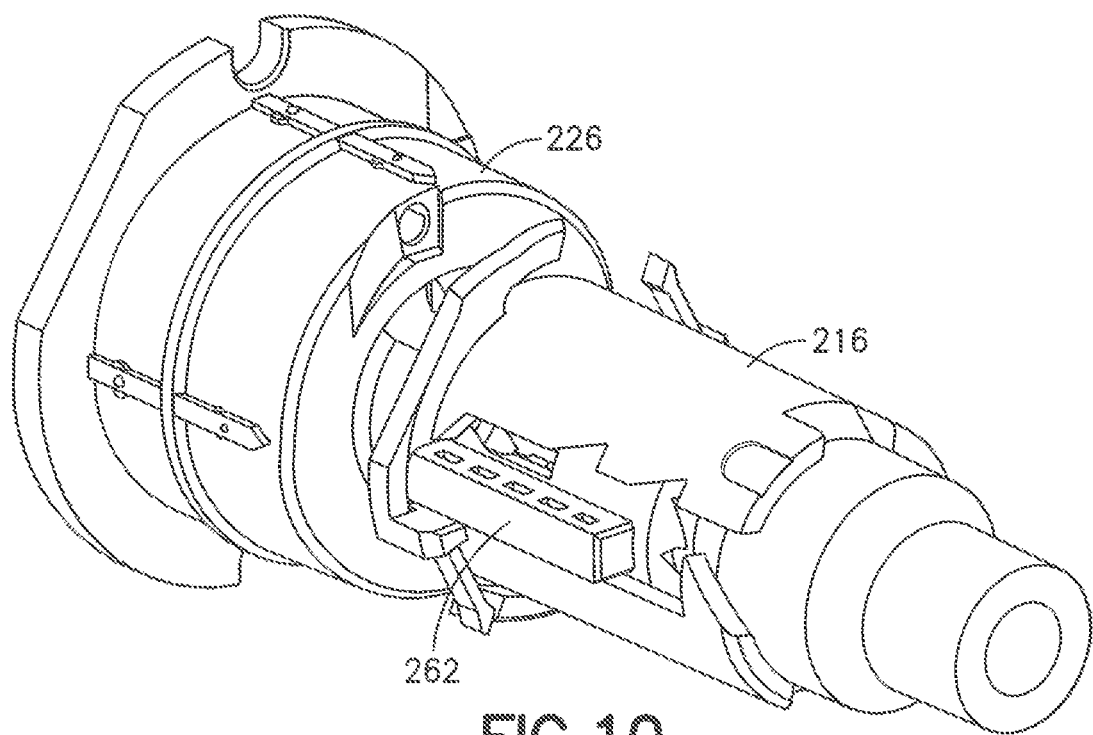
FIG. 10 illustrates a left perspective view of the safety pen needle of FIGS. 7-9 being assembled.

FIG. 9 illustrates the slots 264 of the inner shield 216 being aligned to the locking rails 262 of the needle hub 226 prior to assembly. Subsequently, as illustrated in FIG. 10, the inner shield 216 slides over the needle hub 226 to engage the locking rails 262 in the slots 264. In this position, the locking rails 262 are aligned to openings of the slots 264. Thus, the safety pen needle is in a retracted, unlocked position. The locking rails 262 are exposed because the slots 264 do not enclose the locking rails 262 along a majority of the length of the slot 264.

Figure 11:
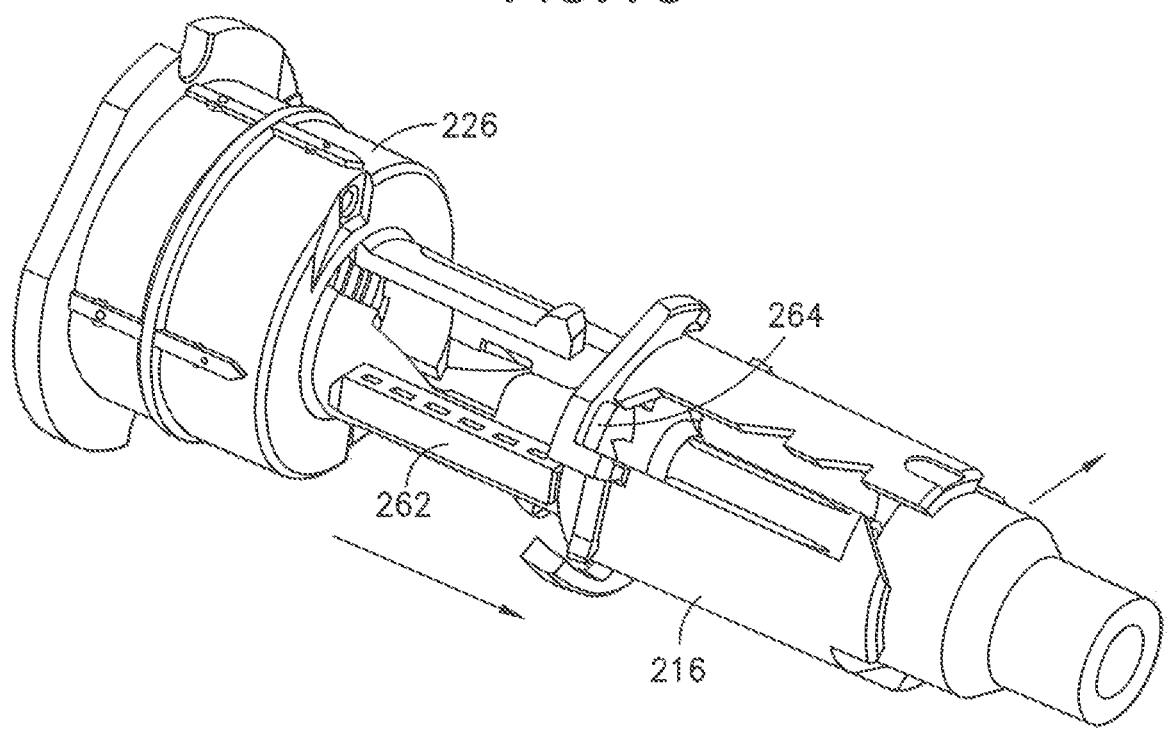
FIG. 11 illustrates a left perspective view of the safety pen needle of FIGS. 7-10 being in an extended position.
Figure 12:
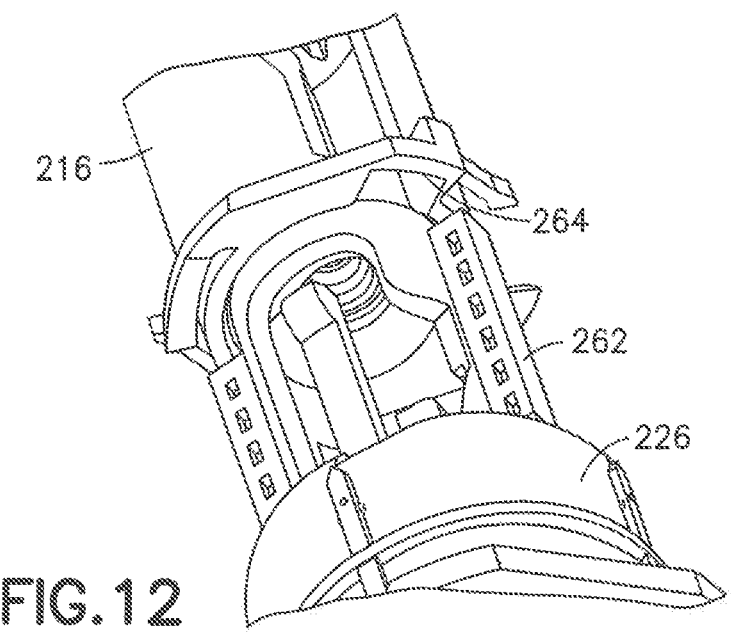
FIG. 12 illustrates a left perspective view of the safety pen needle of FIGS. 7-11 being aligned in the extended position.

FIG. 11 illustrates an extended position of the safety pen needle. Specifically, the inner shield 216 moves forward via a spring force from a spring (not illustrated). The spring is preferably a torsion spring, although other springs are contemplated. FIG. 12 illustrates the slots 264 of the inner shield 216 disengaged from the rails 262 of the needle hub 226.

Figure 13:
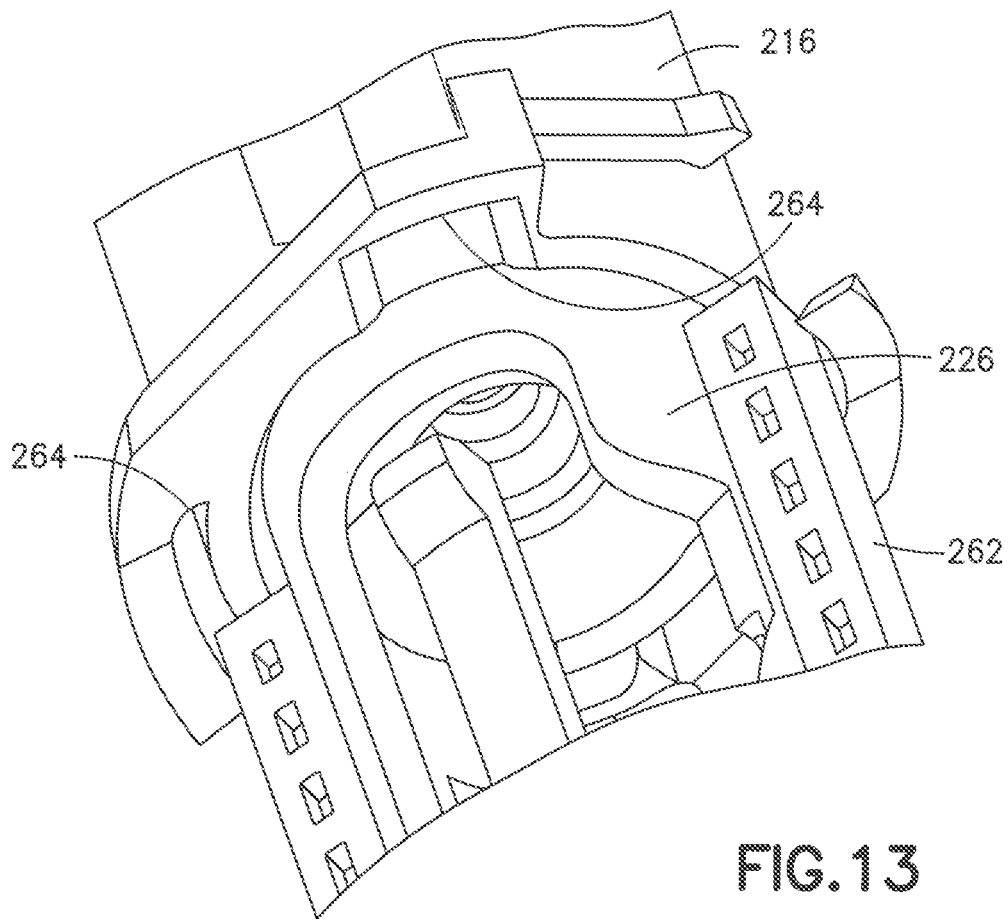
FIG. 13 illustrates a left perspective view of the safety pen needle of FIGS. 7-12 being rotated and locked in the extended position.

At this point, as illustrated in FIG. 13, torsion from the spring causes the inner shield 216 to rotate relative to the needle hub 226. Thus, the rails 262 are misaligned to the slots 264 and the inner shield 216 can no longer slide back over the needle hub 226. That is, the inner shield 216 is not able to return to the retracted, unlocked position. In this manner, the safety pen needle is in an extended, locked position preventing engagement of the inner shield 216 and the needle hub 226.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A safety pen needle assembly comprising:
   a hub;
   a needle cannula engaged to the hub, the needle cannula having a distal end for insertion into a patient, and a proximal end extending into the hub;
   a sleeve surrounding the hub and needle cannula;
   a shield including a window, the shield surrounding the sleeve and movable relative to the sleeve from a first position where the sleeve encloses the needle cannula and hub, to a second position where the needle cannula extends beyond the hub and the sleeve and to a third position where the distal end of the needle cannula is surrounded by the sleeve;
   a locking mechanism that engages the shield to the hub to prevent further use of the needle cannula; and
   a spring urging the shield to move relative to the sleeve from the second position to the third position, wherein the window indicates when the needle cannula is extended in the second position via an indicia on the hub and indicates when the locking mechanism is activated in the third position.

2. The safety pen needle assembly of claim 1, wherein the sleeve or hub is white through the window in the first position.

3. The safety pen needle assembly of claim 1, wherein the sleeve or hub is green through the window in the second position.

4. The safety pen needle assembly of claim 1, wherein the sleeve or hub is red through the window in the third position.

5. The safety pen needle assembly of claim 1, wherein the sleeve or hub displays numbers, patterns, textures and/or symbols through the window to indicate the first, second and third positions.

6. The safety pen needle assembly of claim 1, wherein the first position is an unlocked position where the shield is free to move to expose or cover the needle cannula.

7. The safety pen needle assembly of claim 1, wherein the third position is a locked position where the shield is locked in place to fixedly cover the needle cannula.

8. The safety pen needle assembly of claim 1, wherein the needle cannula is retracted and covered by the hub in the first and third positions.

9. The safety pen needle assembly of claim 1, further comprising a smart ring having electrical contacts or sensors that determine two or more of a position of the shield, needle insertion and needle exposure time, needle insertion rate and needle exposure rate, the number of injections performed, time intervals between injections or the number of needles used or available for injection.

10. The safety pen needle assembly of claim 9, wherein the smart ring communicates with a smart device.

11. The safety pen needle assembly of claim 10, wherein the smart ring communicates a ready, fully deployed or safe mode.

12. The safety pen needle assembly of claim 9, wherein the smart ring is disposed at a proximal end of the safety pen needle assembly.

13. A medication delivery safety pen needle assembly comprising:
    a medication delivery pen; and
    the safety pen needle assembly of claim 9, wherein the smart ring is disposed at a distal end of the medication delivery pen and at a proximal end of the safety pen needle assembly.

14. The safety pen needle assembly of claim 1, wherein the shield includes slots that engage rails on the hub in a retracted, unlocked position.

15. The safety pen needle assembly of claim 14, wherein the slots are not aligned to the rails in an extended, locked position.

16. The safety pen needle assembly of claim 14, further comprising a second spring that rotates the shield with respect to the hub to misalign the slots to the rails.

* * * * *